(12) United States Patent
Aruga et al.

(10) Patent No.: US 11,578,224 B2
(45) Date of Patent: *Feb. 14, 2023

(54) INK SET

(71) Applicant: Seiko Epson Corporation, Tokyo (JP)

(72) Inventors: Tomohiro Aruga, Matsumoto (JP); Shintaro Hama, Matsumoto (JP); Kiyomi Kumamoto, Shiojiri (JP)

(73) Assignee: SEIKO EPSON CORPORATION ( * ) Notice: Subject to any disclaimer, the term of this patent is extended or adjusted under 35 U.S.C. 154(b) by 0 days.

This patent is subject to a terminal disclaimer.

(21) Appl. No.: 16/776,657

(22) Filed: Jan. 30, 2020

(65) Prior Publication Data
US 2020/0248023 A1  Aug. 6, 2020

(30) Foreign Application Priority Data
Jan. 31, 2019  (JP) .............. JP2019-015327

(51) Int. Cl.
| C09D 11/38 | (2014.01) |
| C09D 11/40 | (2014.01) |
| C07F 1/08 | (2006.01) |
| C07D 311/84 | (2006.01) |
| C07D 401/14 | (2006.01) |
| C07D 251/54 | (2006.01) |

(52) U.S. Cl.
CPC .......... C09D 11/38 (2013.01); C07D 251/54 (2013.01); C07D 311/84 (2013.01); C07D 401/14 (2013.01); C07F 1/08 (2013.01); C09D 11/40 (2013.01)

(58) Field of Classification Search
None
See application file for complete search history.

(56) References Cited

U.S. PATENT DOCUMENTS

| 7,503,967 B2 | 3/2009 | Matsui et al. |
| 8,512,462 B2 | 8/2013 | Matsui et al. |
| 8,741,045 B2 | 6/2014 | Kawaguchi et al. |

| 2012/0301685 A1 | 11/2012 | Iseki et al. |
| 2013/0002757 A1 | 1/2013 | Aruga et al. |
| 2016/0032125 A1 | 2/2016 | Ohor et al. |

FOREIGN PATENT DOCUMENTS

| CN | 102796416 A | 11/2012 |
| CN | 105315794 A | 2/2016 |
| EP | 3533841 A1 | 9/2019 |
| JP | 2009-067833 A | 4/2009 |
| JP | 2013-010825 A | 1/2013 |
| JP | 2013-112729 A | 6/2013 |
| JP | 2017-171753 A | 9/2017 |
| WO | 2018-079442 A1 | 5/2018 |

OTHER PUBLICATIONS

U.S. Appl. No. 16/776,717, filed Jan. 30, 2020, Shintaro Hama et al.

*Primary Examiner* — Clinton A Brooks
(74) *Attorney, Agent, or Firm* — Harness, Dickey & Pierce, P.L.C.

(57) ABSTRACT

An ink set includes a first ink containing the compound represented by formula (y-1) or its salt, a second ink containing one or two or more of the compound represented by formula (m-1) or its salt, the compound represented by formula (m-2) or its salt, a compound represented by formula (m-3) or its salt, and the compound represented by formula (m-4) or its salt, and a third ink containing one or two or more of a compound represented by formula (c-1) or its salt, the compound represented by formula (c-2) or its salt, the compound represented by formula (c-3) or its salt, a compound represented by formula (c-4) or its salt, and the compound represented by formula (c-5) or its salt.

[Chem. 1]

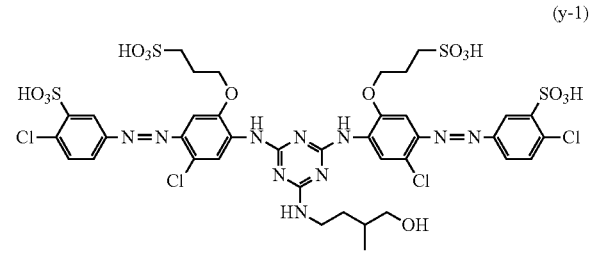

4 Claims, No Drawings

INK SET

The present application is based on, and claims priority from, JP Application Serial Number 2019-015327, filed Jan. 31, 2019, the disclosure of which is hereby incorporated by reference herein in its entirety.

BACKGROUND

1. Technical Field

The present disclosure relates to an ink set.

2. Related Art

In ink jet technology, types of ink sets are used to record images. Each ink in an ink set contains multiple ingredients and, to produce an image in a desired color, contains a colorant, such as a dye or pigment.

Inks in an ink set need to achieve performance suitable for the applications and environments in which the ink set is used. An example of a requirement is that the inks should be resistant to damage from stimuli present in the setting, such as ozone and water, enough that images recorded with the inks will not discolor, fade, or experience any similar defect.

An image discolors and fades usually because of the colorants contained in the inks with which the image is made. Thus efforts have been made to improve colorants in inks, and an example is JP-A-2013-112729. JP-A-2013-112729 proposes using a yellow or yellowish ink that contains particular type(s) of dye(s) and thereby recording an image superior in color reproduction, moisture resistance, and resistance to gases and also excellent in balance between colors.

Inks in an ink set form a meniscus while in the nozzles of an ink jet head. The inks can therefore dry near the end of the nozzles, whether the ink jet apparatus is in use or not. The yellow or yellowish dyes described in JP-A-2013-112729 are highly hydrophilic, and their solubility in ink is more sensitive than that of other similar dyes to changes in the water content of the ink. The dyes described in JP-A-2013-112729 are therefore disadvantageous in that they often cause the ink jet head used therewith to clog up. There is a need for an ink set that is good in color reproduction and unlikely to cause clogging.

SUMMARY

A form of an ink set according to an aspect of the present disclosure includes a first ink containing the compound represented by formula (y-1) below or a salt thereof,

[Chem. 1]

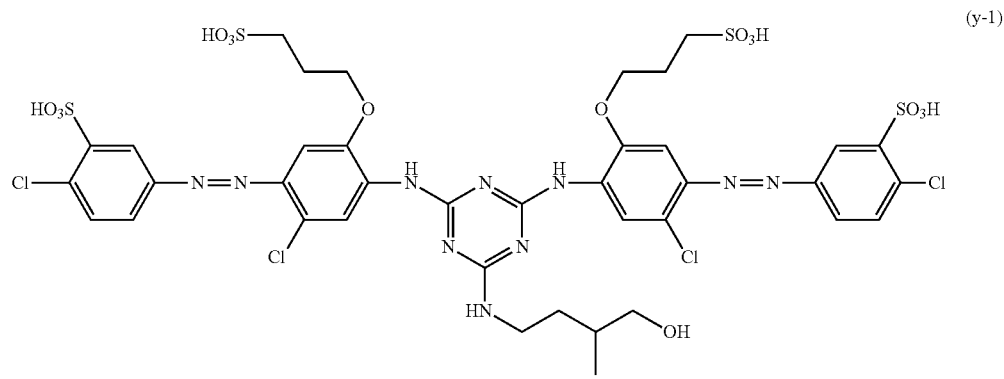

(y-1)

a second ink containing one or two or more of the compound represented by formula (m-1) below or a salt thereof,
[Chem. 2]
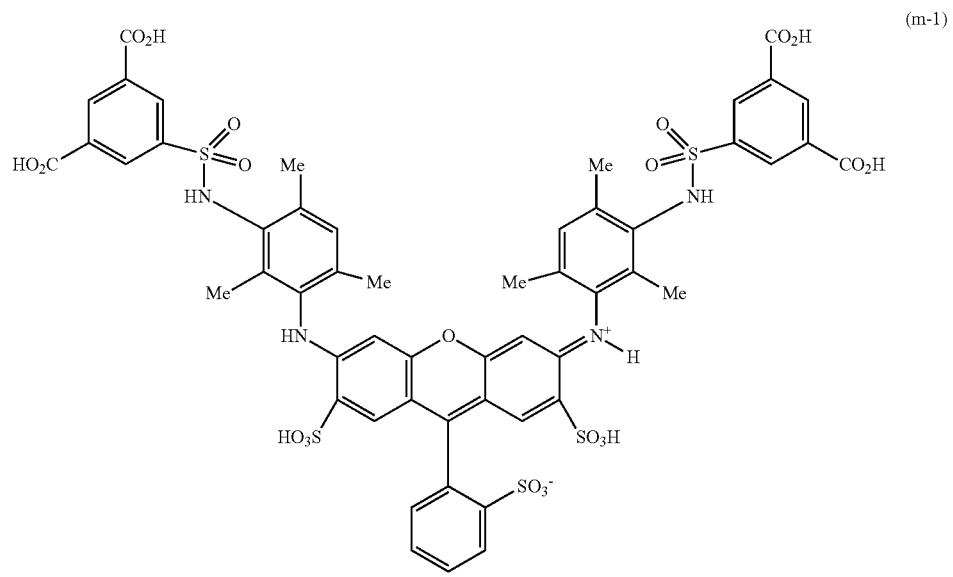
(m-1)
the compound represented by formula (m-2) below or a salt thereof,
[Chem. 3]
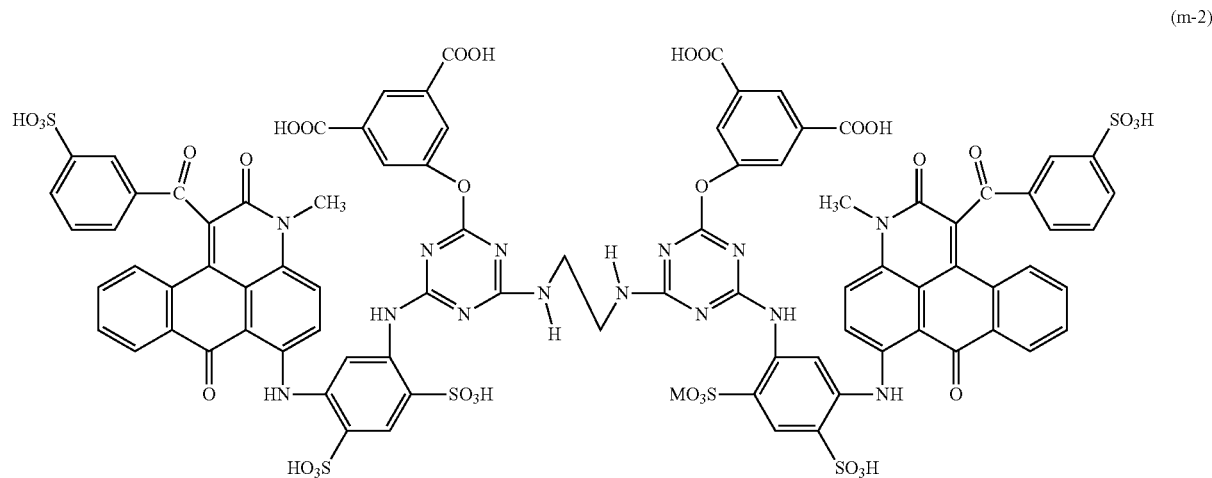
(m-2)

a compound represented by formula (m-3) below or a salt thereof,

[Chem. 4]

(m-3)

where $R^1$, $R^5$, $R^6$, and $R^{10}$ each independently represent an alkyl group, $R^3$ and $R^8$ each independently represent a hydrogen atom, an alkyl group, an alkoxy group, or an aryloxy group, and an alkyl group, an alkoxy group, and an aryloxy group may have at least one type of substituent selected from the group of types of substituents consisting of alkyl, aryl, arylalkyl, hydroxyl, carbamoyl, sulfamoyl, alkoxy, cyano, halogen, and ionic groups, $R^2$, $R^4$, $R^7$, and $R^9$ each independently represent a hydrogen atom or an acylamino group represented by formula (m-3') below, with at least one of $R^2$, $R^4$, $R^7$, and $R^9$ being an acylamino group represented by formula (m-3') below, Z represents a $SO_3H$ group, $SO_3M$ group, where M represents an ammonium ion or alkali metal ion, or sulfamoyl group, n represents an integer of 0 to 3 when at least one of $R^2$, $R^3$, $R^4$, $R^7$, $R^8$, and $R^9$ is substituted with an ionic group, and an integer of 1 to 3 when not, and Z, when present, is in place of at least one aromatic hydrogen atom,

[Chem. 5]

(m-3')

where $R^{11}$ represents an alkyl group, a cycloalkyl group, an aryl group, an arylalkyl group, an alkenyl group, or a heterocyclic group, and an alkyl group, a cycloalkyl group, an aryl group, an arylalkyl group, an alkenyl group, and a heterocyclic group may have at least one type of substituent selected from the group of types of substituents consisting of alkyl, aryl, arylalkyl, alkenyl, alkoxy, cyano, alkylamino, sulfoalkyl, carbamoyl, sulfamoyl, sulfonylamino, halogen, and ionic groups, and * represents a site for binding with the aromatic ring or rings in formula (m-3), and the compound represented by formula (m-4) below or a salt thereof,

[Chem. 6]

(m-4)

and a third ink containing one or two or more of a compound represented by formula (c-1) below or a salt thereof,

[Chem. 7]

(c-1)

where $0 \leq b \leq 4$, $0 \leq c \leq 4$, and $1 \cdot (b+c) \leq 4$, where b+c represents an integer, and rings $A^1$, $A^2$, and $A^3$ are each selected from a benzene ring, a 2,3-pyridine ring, and a 3,2-pyridine ring, with at least one of rings $A^1$, $A^2$, and $A^3$ being a 2,3-pyridine ring or 3,2-pyridine ring, and rings $A^1$, $A^2$, and $A^3$ may be the same or different, the compound represented by formula (c-2) below or a salt thereof,

[Chem. 8]

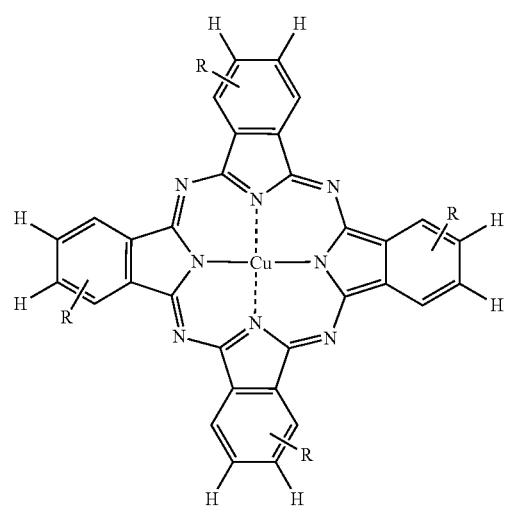

(c-2)

the compound represented by formula (c-3) below or a salt thereof,

[Chem. 9]

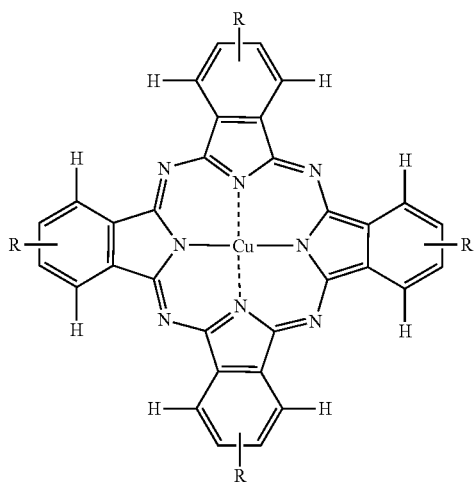

(c-3)

a compound represented by formula (c-4) below or a salt thereof,

[Chem. 10]

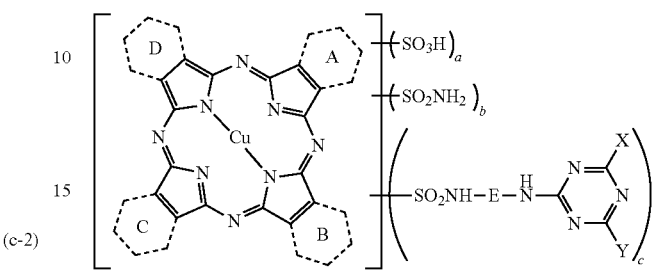

(c-4)

where rings A, B, C, and D are each independently an aromatic six-membered ring, with at least one of rings A, B, C, and D being a pyridine ring or pyrazine ring, E is an alkylene group, X is a sulfo-substituted anilino group, carboxy-substituted anilino group, or phosphono-substituted anilino group, and the substituted anilino group may further have one to four substituents selected from the group consisting of a sulfonic acid group, a carboxy group, a phosphono group, a sulfamoyl group, a carbamoyl group, a hydroxy group, an alkoxy group, an amino group, an alkylamino group, a dialkylamino group, an arylamino group, a diarylamino group, an acetylamino group, a ureido group, an alkyl group, a nitro group, a cyano group, a halogen, an alkylsulfonyl group, and an alkylthio group, Y is a hydroxy group or amino group, and $0.0 \leq a \leq 2.0$, $0.0 \leq b \leq 3.0$, $0.1 \leq c \leq 3.0$, and $1.0 \leq a+b+c \leq 4.0$, and the compound represented by formula (c-5) below or a salt thereof.

[Chem. 11]

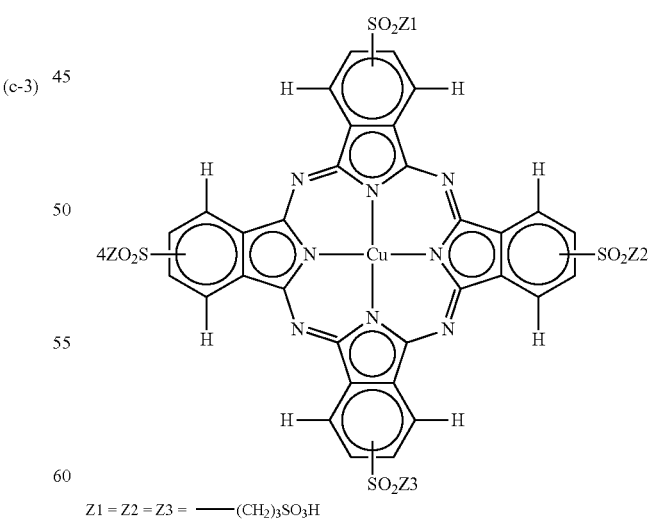

(c-5)

In the above form of an ink set, the first ink may further contain the compound represented by formula (y-2) below or a salt thereof.

[Chem. 12]

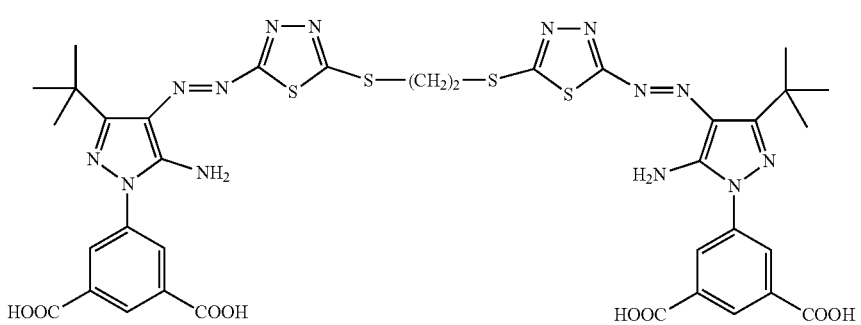

(y-2)

In any of the above forms of an ink set, the second ink may contain the compound represented by formula (m-2) or a salt thereof.

In any of the above forms of an ink set, the third ink may contain the compound represented by formula (c-2) or a salt thereof and the compound represented by formula (c-3) or a salt thereof.

DESCRIPTION OF EXEMPLARY EMBODIMENTS

The following describes embodiments of the present disclosure. The following embodiments are descriptions of examples of the disclosure. The disclosure is never limited to these embodiments and includes variations implemented within the gist of the disclosure. Not all the configurations described below are essential for the disclosure.

1. Ink Set

An ink set according to this embodiment includes a first ink, a second ink, and a third ink. There may be other inks in the ink set.
1.1. First Ink In the ink set according to this embodiment, a first ink is included. The first ink in the ink set is included in the ink set as, for example, a yellow dye ink.

The first ink contains the compound represented by formula (y-1) or its salt.

In formula (y-1), the compound has four sulfonic acid groups that may each independently be in the sulfonate form. Examples of counterions in a salt of the compound represented by formula (y-1) include the hydrogen ion (proton), lithium, sodium, potassium, and ammonium, and the salt may have counterions of the same species or different counterions at its four sulfonic acid groups. The compound represented by formula (y-1) or its salt is a yellow or yellowish dye. "The compound represented by formula (y-1) or its salt" may hereinafter be referred to simply as "a (y-1) dye."

After studying a wide variety of yellow and yellowish dye inks, the inventors found that inks made with a (y-1) dye are unlikely to cause the nozzles of an ink jet head used therewith to clog up. The underlying mechanism remains to be clearly understood, but the inventors presumes that the effect owes to the hydrophobicity of the 3-methyl-4-hydroxy-amino group bound to the triazine ring in the (y-1) dye.

The (y-1) dyes, moreover, have good color strength compared with other yellow or yellowish dyes. The presence of the first ink in the ink set according to this embodiment therefore helps extend the gamut, represented by the gamut volume for example, of the ink set.

1.1.1. Other Dyes

Besides the (y-1) dye, the first ink may further contain the compound represented by formula (y-2) below or its salt.

[Chem. 13]

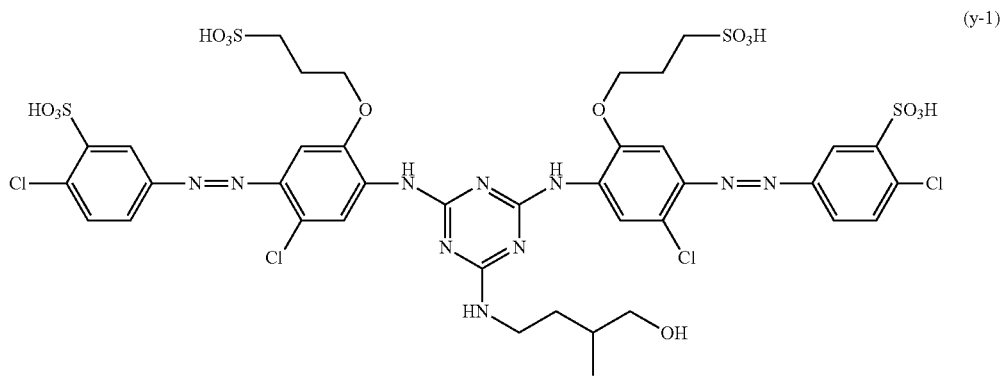

(y-1)

[Chem. 14]

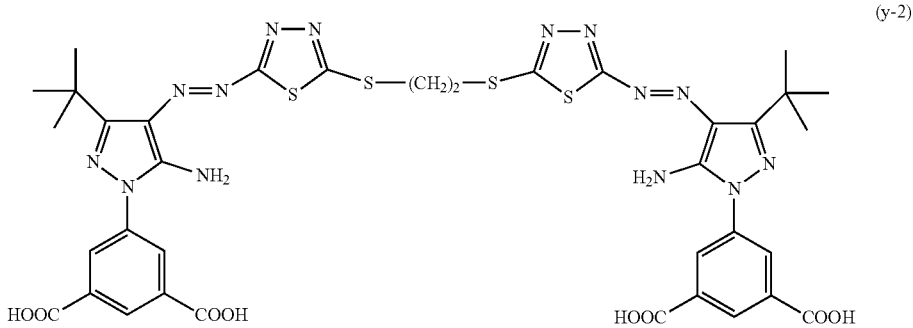

(y-2)

In formula (y-2), the compound has four carboxy groups that may each independently be in the carboxylate form. Examples of counterions in a salt of the compound represented by formula (y-2) include the hydrogen ion (proton), lithium, sodium, potassium, and ammonium, and the salt may have counterions of the same species or different counterions at its four carboxy groups. The compound represented by formula (y-2) or its salt is a yellow or yellowish dye. "The compound represented by formula (y-2) or its salt" may hereinafter be referred to simply as "a (y-2) dye."

Besides the (y-1) dye, the first ink may further contain the compound represented by formula (y-3) or its salt.

The (y-1) dyes exhibit a yellow or yellowish color but are faintly tinged red. The (y-2) dyes and the (y-3) dyes are yellow or yellowish and faintly tinged green. The use of any of these dyes in the first ink therefore helps further extend the gamut of the ink set.

The first ink may contain other yellow or yellowish dyes, but they would probably have little effect in extending the gamut. Even when any such yellow or yellowish dye is contained in the first ink, it remains preferred to ensure that the (y-1) dye content of the first ink is 40.0% by mass or more and 99.0% by mass or less of the total mass of dyes in the first ink.

1.1.2. Extra Ingredients

[Chem. 15]

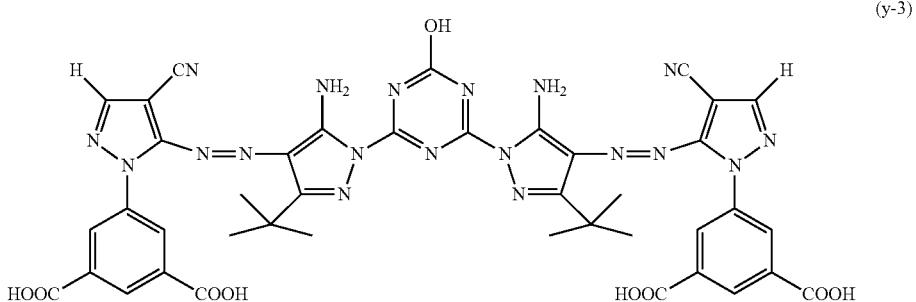

(y-3)

In formula (y-3), the compound has four carboxy groups that may each independently be in the carboxylate form. Examples of counterions in a salt of the compound represented by formula (y-3) include the hydrogen ion (proton), lithium, sodium, potassium, and ammonium, and the salt may have counterions of the same species or different counterions at its four carboxy groups. The compound represented by formula (y-3) or its salt is a yellow or yellowish dye. "The compound represented by formula (y-3) or its salt" may hereinafter be referred to simply as "a (y-3) dye."

The first ink may contain one or two or more dyes selected from the (y-2) dyes and the (y-3) dyes. When it does, however, it is preferred that the (y-1) dye content of the first ink be 40.0% by mass or more and 99.0% by mass or less, more preferably 50.0% by mass or more and 90.0% by mass or less, even more preferably 60.0% by mass or more and 90.0% by mass or less of the total mass of dyes in the first ink.

The first ink according to this embodiment may contain a surfactant, an organic solvent, water, and other ingredients.

(1) Surfactant

The first ink may contain a surfactant. The surfactant reduces the surface tension of the first ink, thereby improving the wettability of the ink on a recording medium or substrate. Among surfactants, acetylene glycol surfactants, silicone surfactants, and fluorosurfactants are particularly preferred for use.

An acetylene glycol surfactant can be of any kind, but examples include Surfynol 104, 104E, 104H, 104A, 104BC, 104DPM, 104PA, 104PG-50, 104S, 420, 440, 465, 485, SE, SE-F, 504, 61, DF37, CT111, CT121, CT131, CT136, TG, GA, and DF110D (all are trade names; Air Products and Chemicals), OLFINE B, Y, P, A, STG, SPC, E1004, E1010, PD-001, PD-002W, PD-003, PD-004, EXP. 4001, EXP. 4036, EXP. 4051, AF-103, AF-104, AK-02, SK-14, and AE-3 (all are trade names; Nissin Chemical Industry), and ACETYLENOL E00, E00P, E40, and E100 (all are trade names; Kawaken Fine Chemicals).

A silicone surfactant can be of any kind, but an example of a preferred one is a polysiloxane compound. The polysiloxane compound can be of any kind, but an example is a polyether-modified organosiloxane. Examples of commercially available polyether-modified organosiloxanes include BYK-306, BYK-307, BYK-333, BYK-341, BYK-345, BYK-346, and BYK-348 (trade names; BYK Japan) and KF-351A, KF-352A, KF-353, KF-354L, KF-355A, KF-615A, KF-945, KF-640, KF-642, KF-643, KF-6020, X-22-4515, KF-6011, KF-6012, KF-6015, and KF-6017 (trade names; Shin-Etsu Chemical).

A fluorosurfactant is preferably a fluorine-modified polymer. Specific examples include BYK-3440 (BYK Japan), SURFLON S-241, S-242, and S-243 (trade names; AGC Seimi Chemical), and FTERGENT 215M (NEOS).

The first ink may contain multiple surfactants. When the first ink contains surfactant(s), the surfactant content is preferably 0.1% by mass or more and 2.0% by mass or less, more preferably 0.2% by mass or more and 1.5% by mass or less, even more preferably 0.3% by mass or more and 1.0% by mass or less of the total mass.

(2) Organic Solvent

The first ink may contain an organic solvent. Although the first ink may be organic solvent-free, the use of an organic solvent makes it easier to achieve quick drying combined with ejection stability. Water-soluble organic solvents are preferred.

A function of the organic solvent is to improve the wettability of the first ink on a recording medium and to enhance the water retention of the first ink. Examples of organic solvents include esters, alkylene glycol ethers, cyclic esters, nitrogen-containing solvents, and polyhydric alcohols. Examples of nitrogen-containing solvents include cyclic amides and acyclic amides. Examples of acyclic amides include alkoxyalkylamides.

Examples of esters include glycol monoacetates, such as ethylene glycol monomethyl ether acetate, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, propylene glycol monomethyl ether acetate, dipropylene glycol monomethyl ether acetate, and methoxybutyl acetate, and glycol diesters, such as ethylene glycol diacetate, diethylene glycol diacetate, propylene glycol diacetate, dipropylene glycol diacetate, ethylene glycol acetate propionate, ethylene glycol acetate butyrate, diethylene glycol acetate butyrate, diethylene glycol acetate propionate, diethylene glycol acetate butyrate, propylene glycol acetate propionate, propylene glycol acetate butyrate, dipropylene glycol acetate butyrate, and dipropylene glycol acetate propionate.

An alkylene glycol ether can be any monoether or diether of an alkylene glycol, preferably an alkyl ether. Specific examples include alkylene glycol monoalkyl ethers, such as ethylene glycol monomethyl ether, ethylene glycol monoethyl ether, ethylene glycol monoisopropyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, triethylene glycol monobutyl ether, tetraethylene glycol monomethyl ether, tetraethylene glycol monoethyl ether, tetraethylene glycol monobutyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, and tripropylene glycol monobutyl ether, and alkylene glycol dialkyl ethers, such as ethylene glycol dimethyl ether, ethylene glycol diethyl ether, ethylene glycol dibutyl ether, diethylene glycol dimethyl ether, diethylene glycol diethyl ether, diethylene glycol dibutyl ether, diethylene glycol methyl ethyl ether, diethylene glycol methyl butyl ether, triethylene glycol dimethyl ether, triethylene glycol diethyl ether, triethylene glycol dibutyl ether, triethylene glycol methyl butyl ether, tetraethylene glycol dimethyl ether, tetraethylene glycol diethyl ether, tetraethylene glycol dibutyl ether, propylene glycol dimethyl ether, propylene glycol diethyl ether, dipropylene glycol dimethyl ether, dipropylene glycol diethyl ether, and tripropylene glycol dimethyl ether.

Examples of cyclic esters include cyclic esters (lactones) such as β-propiolactone, γ-butyrolactone, δ-valerolactone, ε-caprolactone, γ-butyrolactone, β-valerolactone, γ-valerolactone, β-hexanolactone, γ-hexanolactone, δ-hexanolactone, β-heptanolactone, γ-heptanolactone, δ-heptanolactone, ε-heptanolactone, γ-octanolactone, δ-octanolactone, ε-octanolactone, δ-nonalactone, ε-nonalactone, and ε-decanolactone and compounds resulting from the substitution of hydrogen(s) of the methylene group next to the carbonyl group of these lactones with a C1 to C4 alkyl group.

Examples of alkoxyalkylamides include 3-methoxy-N,N-dimethylpropionamide, 3-methoxy-N,N-diethylpropionamide, 3-methoxy-N,N-methylethylpropionamide, 3-ethoxy-N,N-dimethylpropionamide, 3-ethoxy-N,N-diethylpropionamide, 3-ethoxy-N,N-methylethylpropionamide, 3-n-butoxy-N,N-dimethylpropionamide, 3-n-butoxy-N,N-diethylpropionamide, 3-n-butoxy-N,N-methylethylpropionamide, 3-n-propoxy-N,N-dimethylpropionamide, 3-n-propoxy-N,N-diethylpropionamide, 3-n-propoxy-N,N-methylethylpropionamide, 3-isopropoxy-N,N-dimethylpropionamide, 3-isopropoxy-N,N-diethylpropionamide, 3-isopropoxy-N,N-methylethylpropionamide, 3-tert-butoxy-N,N-dimethylpropionamide, 3-tert-butoxy-N,N-diethylpropionamide, and 3-tert-butoxy-N,N-methylethylpropionamide.

Examples of cyclic amides include lactams, such as pyrrolidones including 2-pyrrolidone, 1-methyl-2-pyrrolidone, 1-ethyl-2-pyrrolidone, 1-propyl-2-pyrrolidone, and 1-butyl-2-pyrrolidone. 2-Pyrrolidone is particularly preferred.

It is also preferred to use an alkoxyalkylamide, a type of acyclic amide. An alkoxyalkylamide is a compound represented by formula (1) below.

$$R^1-O-CH_2CH_2-(C=O)-NR^2R^3 \qquad (1)$$

In formula (1) above, $R^1$ denotes a C1 to C4 alkyl group, and $R^2$ and $R^3$ each independently denote a methyl or ethyl group. The "C1 to C4 alkyl group" can be a linear or branched alkyl group. To name a few, it can be a methyl, ethyl, n-propyl, isopropyl, n-butyl, sec-butyl, isobutyl, or tert-butyl group. One of those compounds represented by formula (1) above may be used alone, or two or more may be used as a mixture.

Examples of polyhydric alcohols includes 1,2-alkanediols (e.g., alkanediols such as ethylene glycol, propylene glycol (aka: propane-1,2-diol), triethylene glycol, 1,2-butanediol, 1,2-pentanediol, 1,2-hexanediol, 1,2-heptanediol, and 1,2-octanediol) and polyhydric alcohols other than 1,2-alkanediols (polyols) (e.g., diethylene glycol, dipropylene glycol, 1,3-propanediol, 1,3-butanediol (aka: 1,3-butylene glycol), 1,4-butanediol, 1,5-pentanediol, 1,6-hexanediol, 2-ethyl-2-methyl-1,3-propanediol, 2-methyl-2-propyl-1,3-propanediol, 2-methyl-1,3-propanediol, 2,2-dimethyl-1,3-propanediol, 3-methyl-1,3-butanediol, 2-ethyl-1,3-hexanediol, 3-methyl-1,5-pentanediol, 2-methylpentane-2,4-diol, trimethylolpropane, and glycerol).

The first ink may contain one of these organic solvents listed by way of example alone or may contain two or more in combination. When the first ink is made with organic solvent(s), the total percentage of organic solvents to the first ink as a whole is 3.0% by mass or more and 30.0% by mass or less, preferably 5.0% by mass or more and 25.0% by mass or less, more preferably 10.0% by mass or more and 20.0% by mass or less.

(3) Water

The first ink may contain water. Preferably, the first ink is water-based. A water-based composition contains water as a major solvent component. The water may be contained as the primary solvent component and is a component that evaporates away upon drying. Preferably, the water is of a type from which ionic impurities have been removed to the lowest possible levels, such as ion exchange water, ultrafiltered water, reverse osmosis water, distilled water, or any other type of purified water or ultrapure water. The use of sterilized water, for example sterilized by ultraviolet irradiation or adding hydrogen peroxide, is preferred because it helps control fungal and bacterial development when the first ink is stored long. The water content is preferably 75.0% by mass or more, more preferably 80.0% by mass or more and 98% by mass or less, even more preferably 85.0% by mass or more and 95.0% by mass or less of the total mass of the first ink.

(4) Others

The first ink may contain extra ingredients, such as a pH-adjusting agent, an antimold/preservative, a chelating agent, an antirust, a fungicide, an antioxidant, an antireductant, and a drying agent.

Examples of pH-adjusting agents include ureas, amines, morpholines, piperazines, and aminoalcohols, for example a combination of secondary or more aminoalcohols. Examples of ureas include urea, ethylene urea, tetramethylurea, thiourea, 1,3-dimethyl-2-imidazolidinone and similar compounds and betaines (e.g., trimethylglycine, triethylglycine, tripropylglycine, triisopropylglycine, N,N,N-trimethylalanine, N,N,N-triethylalanine, N,N,N-triisopropylalanine, N,N,N-trimethylmethylalanine, carnitine, and acetylcarnitine). Examples of amines include diethanolamine and a triisopropanolamines. The use of a pH-adjusting agent helps, for example, adjust the detergency of the first ink by helping reduce or enhance the dissolution of impurities from elements forming the channel through which the ink flows.

For antimolds/preservatives, examples include PROXEL CRL, PROXEL BDN, PROXEL GXL, PROXEL XL2, PROXEL IB, and PROXEL TN (all are trade names; Lonza). The use of an antimold/preservative ensures better storage properties of the first ink by helping control fungal and bacterial growth.

For chelating agents, examples include ethylenediaminetetraacetic acid (EDTA) and the nitrilotriacetate, hexametaphosphate, pyrophosphate, or metaphosphate of ethylenediamine.

1.2. Second Ink

In the ink set according to this embodiment, a second ink is included. The second ink in the ink set is included in the ink set as, for example, a magenta dye ink. The second ink contains at least one magenta or substantially magenta dye.

1.2.1. Magenta or Substantially Magenta Dye(s)

The second ink according to this embodiment contains, as magenta or substantially magenta dye(s), one or two or more selected from:

the compound represented by formula (m-1) below or its salt;

[Chem. 16]

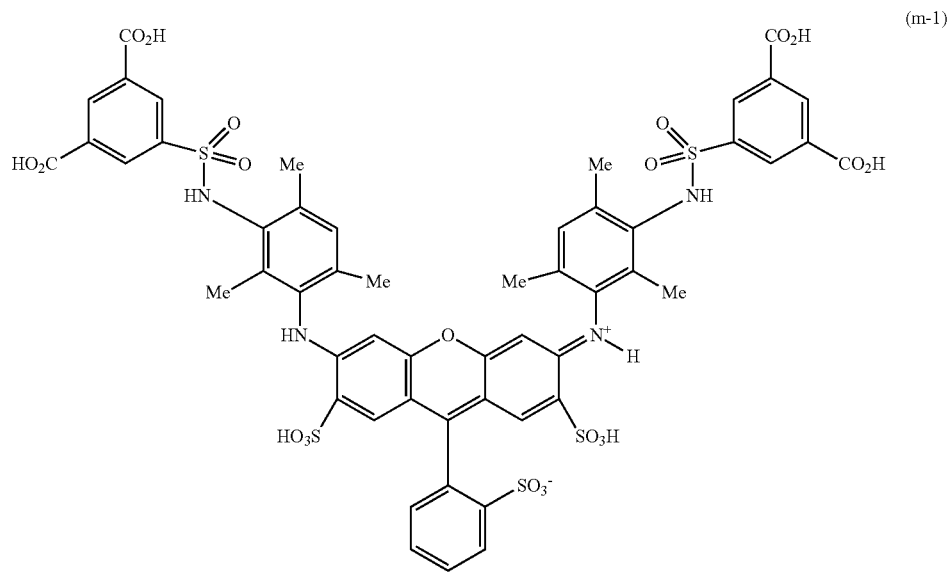

(m-1)

the compound represented by formula (m-2) below or its salt;

[Chem. 17]

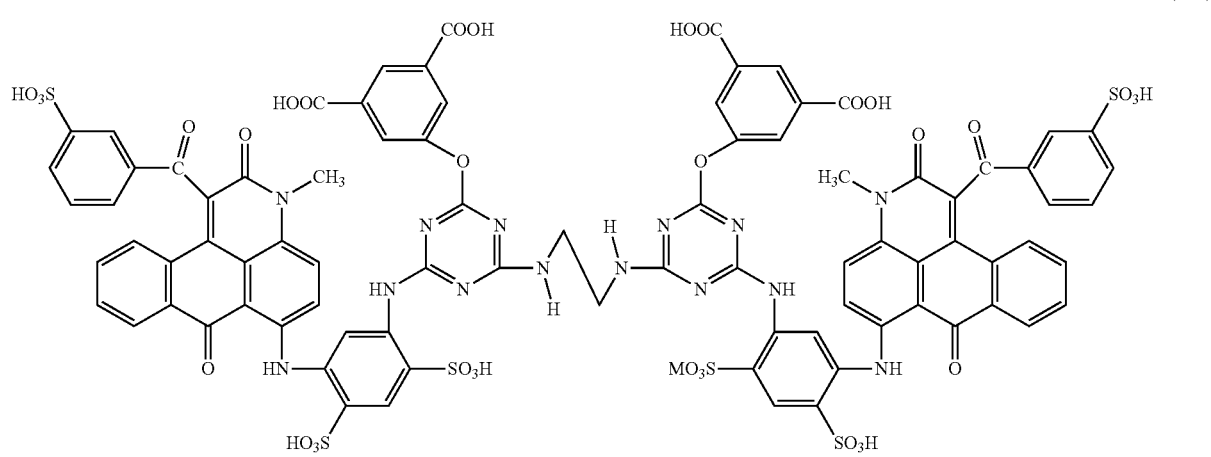

(m-2)

a compound represented by formula (m-3) below or its salt

[Chem. 18]

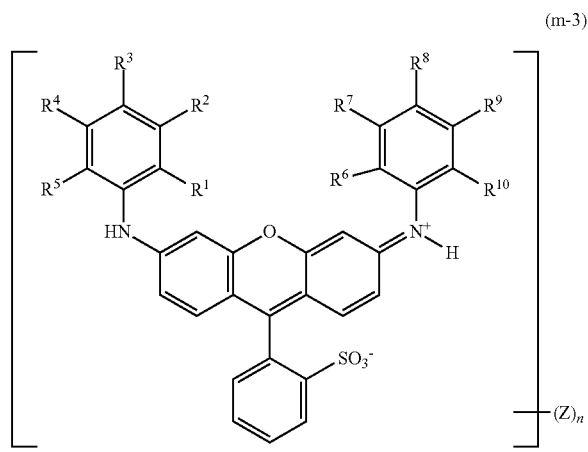

(m-3)

(In formula (m-3), $R^1$, $R^5$, $R^6$, and $R^{10}$ each independently represent an alkyl group. $R^3$ and $R^8$ each independently represent a hydrogen atom, an alkyl group, an alkoxy group, or an aryloxy group, and an alkyl group, an alkoxy group, and an aryloxy group may have at least one type of substituent selected from the group of types of substituents consisting of alkyl, aryl, arylalkyl, hydroxyl, carbamoyl, sulfamoyl, alkoxy, cyano, halogen, and ionic groups. $R^2$, $R^4$, $R^7$, and $R^9$ each independently represent a hydrogen atom or an acylamino group represented by formula (m-3') below, with at least one of $R^2$, $R^4$, $R^7$, and $R^9$ being an acylamino group represented by formula (m-3') below. Z represents a $SO_3H$ group, $SO_3M$ group (where M represents an ammonium ion or alkali metal ion), or sulfamoyl group. n represents an integer of 0 to 3 when at least one of $R^2$, $R^3$, $R^4$, $R^7$, $R^8$, and $R^9$ is substituted with an ionic group, and an integer of 1 to 3 when not, and Z, when present, is in place of at least one aromatic hydrogen atom.)

[Chem. 19]

(m-3')

(In formula (m-3'), $R^{11}$ represents an alkyl group, a cycloalkyl group, an aryl group, an arylalkyl group, an alkenyl group, or a heterocyclic group, and an alkyl group, a cycloalkyl group, an aryl group, an arylalkyl group, an alkenyl group, and a heterocyclic group may have at least one type of substituent selected from the group of types of substituents consisting of alkyl, aryl, arylalkyl, alkenyl, alkoxy, cyano, alkylamino, sulfoalkyl, carbamoyl, sulfamoyl, sulfonylamino, halogen, and ionic groups. * represents a site for binding with the aromatic ring(s) in formula (m-3)); and the compound represented by formula (m-4) below or its salt.

[Chem. 20]

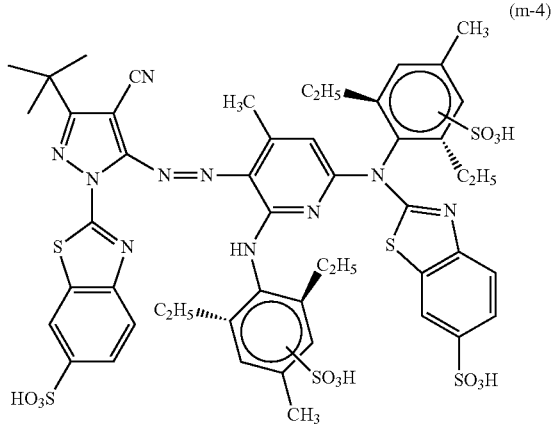

Examples of counterions in a salt of the compound represented by formula (m-1) include the hydrogen ion (proton), lithium, sodium, potassium, and ammonium, and the salt may have counterions of the same species or different counterions at its four carboxy and two sulfonic acid groups. The compound represented by formula (m-1) or its salt is a magenta or substantially magenta dye. "The compound represented by formula (m-1) or its salt" may hereinafter be referred to simply as "an (m-1) dye."

Examples of counterions in a salt of the compound represented by formula (m-2) include the hydrogen ion (proton), lithium, sodium, potassium, and ammonium, and the salt may have counterions of the same species or different counterions at its four carboxy and six sulfonic acid groups. The compound represented by formula (m-2) or its salt is a magenta or substantially magenta dye. "The compound represented by formula (m-2) or its salt" may hereinafter be referred to simply as "an (m-2) dye."

Examples of counterions in a salt of a compound represented by formula (m-3) include the hydrogen ion (proton), lithium, sodium, potassium, and ammonium. A compound represented by formula (m-3) or its salt is a magenta or substantially magenta dye. "A compound represented by formula (m-3) or its salt" may hereinafter be referred to simply as "an (m-3) dye."

Examples of counterions in a salt of the compound represented by formula (m-4) include the hydrogen ion (proton), lithium, sodium, potassium, and ammonium, and the salt may have counterions of the same species or different counterions at its four sulfonic acid groups. The compound represented by formula (m-4) or its salt is a magenta or substantially magenta dye. "The compound represented by formula (m-4) or its salt" may hereinafter be referred to simply as "an (m-4) dye."

The second ink may contain other magenta or substantially magenta dyes. Examples of such extra magenta or substantially magenta dyes include C.I. Direct Red 1, 4, 9, 80, 81, and 225 and C.I. Acid Red 52, 80, 82, 227, 249, 254, and 289.

Even when any such magenta or substantially magenta dye is contained in the second ink, it remains preferred, in light of the area of the gamut, to ensure that the total percentage of (m-1) to (m-4) dyes in the second ink is 40.0% by mass or more and 99.0% by mass or less of the total mass of dyes in the second ink.

1.2.2. Extra Ingredients

The second ink according to this embodiment may contain a surfactant, an organic solvent, water, and other ingredients. These ingredients are as described in the above section of First Ink and are not discussed again.

1.3. Third Ink

In the ink set according to this embodiment, a third ink is included. The third ink in the ink set is included in the ink set as, for example, a cyan dye ink. The third ink contains at least one cyan or substantially cyan dye.

1.3.1. Cyan or Substantially Cyan Dye(s)

The third ink according to this embodiment contains, as cyan or substantially cyan dye(s), one or two or more selected from:

a compound represented by formula (c-1) below or its salt

[Chem. 21]

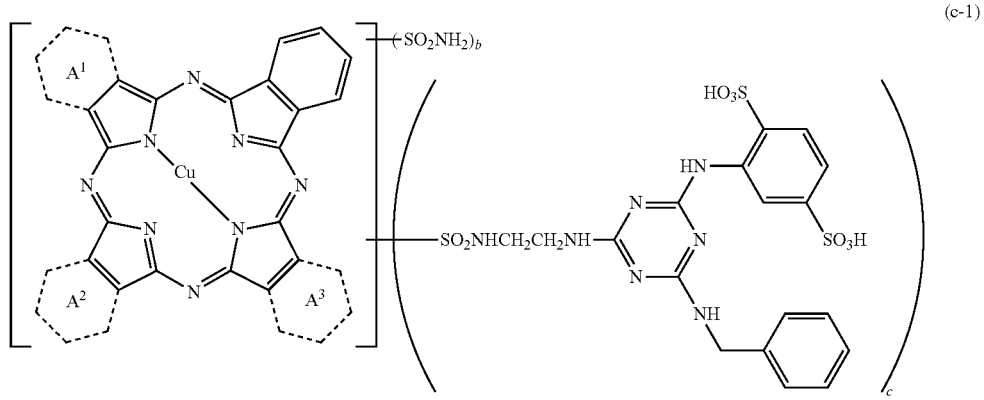

(In formula (c-1), 0≤b≤4, 0≤c≤4, and 1≤(b+c)≤4, where b+c represents an integer; and rings $A^1$, $A^2$, and $A^3$ are each selected from a benzene ring, a 2,3-pyridine ring, and a 3,2-pyridine ring, with at least one of rings $A^1$, $A^2$, and $A^3$ being a 2,3-pyridine ring or 3,2-pyridine ring, and rings $A^1$, $A^2$, and $A^3$ may be the same or different);

the compound represented by formula (c-2) below or its salt;

[Chem. 22]

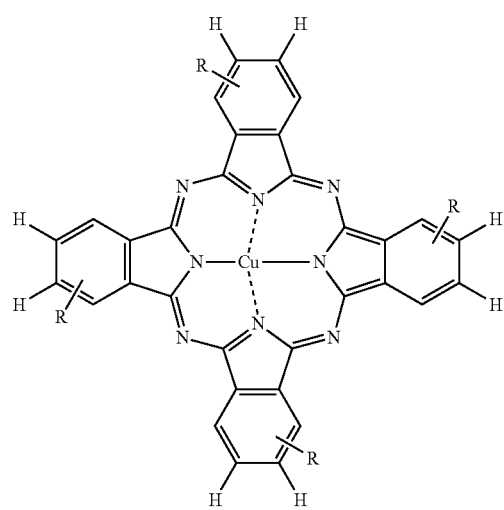

(c-2)

R = —SO$_2$(CH$_2$)$_3$SO$_3$H the compound represented by formula (c-3) below or its salt;

[Chem. 23]

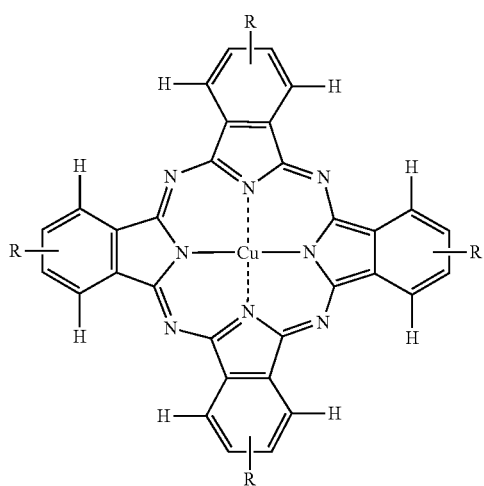

(c-3)

R = —SO$_2$(CH$_2$)$_3$SO$_3$H/ —SO$_2$(CH$_2$)$_3$SO$_2$NHCH$_2$CH(OH)CH$_3$

[2/2]

a compound represented by formula (c-4) below or its salt

[Chem. 24]

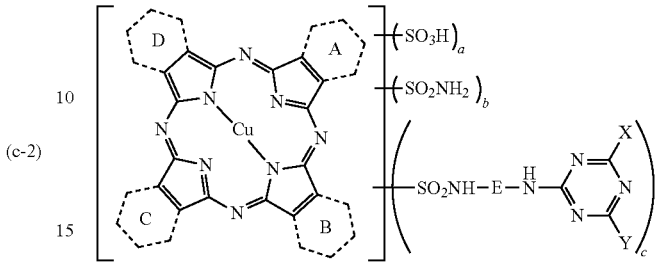

(c-4)

(In formula (c-4), rings A, B, C, and D are each independently an aromatic six-membered ring, with at least one of rings A, B, C, and D being a pyridine ring or pyrazine ring. E is an alkylene group. X is a sulfo-substituted anilino group, carboxy-substituted anilino group, or phosphono-substituted anilino group, and the substituted anilino group may further have one to four substituents selected from the group consisting of a sulfonic acid group, a carboxy group, a phosphono group, a sulfamoyl group, a carbamoyl group, a hydroxy group, an alkoxy group, an amino group, an alkylamino group, a dialkylamino group, an arylamino group, a diarylamino group, an acetylamino group, a ureido group, an alkyl group, a nitro group, a cyano group, a halogen, an alkylsulfonyl group, and an alkylthio group. Y is a hydroxy group or amino group. $0.0 \le a \le 2.0$, $0.0 \le b \le 3.0$, $0.1 \le c \le 3.0$, and $1.0 \le a+b+c \le 4.0$); and the compound represented by formula (c-5) below or its salt.

[Chem. 25]

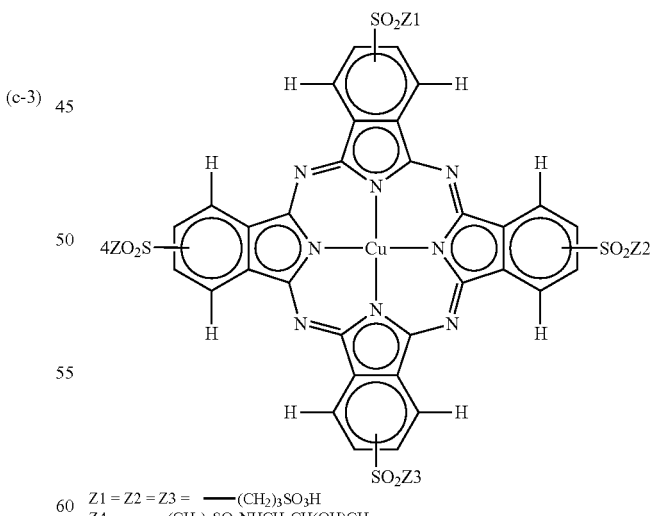

(c-5)

Z1 = Z2 = Z3 = —(CH$_2$)$_3$SO$_3$H
Z4 = —(CH$_2$)$_3$SO$_3$NHCH$_2$CH(OH)CH$_3$

Examples of counterions in a salt of a compound represented by formula (c-1) include the hydrogen ion (proton), lithium, sodium, potassium, and ammonium, and the salt may have counterions of the same species or different counterions at its sulfonic acid groups. A compound represented by formula (c-1) or its salt is a cyan or substantially cyan dye. "A compound represented by formula (c-1) or its salt" may hereinafter be referred to simply as "a (c-1) dye."

Examples of counterions in a salt of the compound represented by formula (c-2) include the hydrogen ion (proton), lithium, sodium, potassium, and ammonium, and the salt may have counterions of the same species or different counterions at its four sulfonic acid groups. The compound represented by formula (c-2) or its salt is a cyan or substantially cyan dye. "The compound represented by formula (c-2) or its salt" may hereinafter be referred to simply as "a (c-2) dye."

Examples of counterions in a salt of the compound represented by formula (c-3) include the hydrogen ion (proton), lithium, sodium, potassium, and ammonium, and the salt may have counterions of the same species or different counterions at its two sulfonic acid groups. The compound represented by formula (c-3) or its salt is a cyan or substantially cyan dye. "The compound represented by formula (c-3) or its salt" may hereinafter be referred to simply as "a (c-3) dye."

Examples of counterions in a salt of a compound represented by formula (c-4) include the hydrogen ion (proton), lithium, sodium, potassium, and ammonium. A compound represented by formula (c-4) or its salt is a cyan or substantially cyan dye. "A compound represented by formula (c-4) or its salt" may hereinafter be referred to simply as "a (c-4) dye."

Examples of counterions in a salt of the compound represented by formula (c-5) include the hydrogen ion (proton), lithium, sodium, potassium, and ammonium, and the salt may have counterions of the same species or different counterions at its three sulfonic acid groups. The compound represented by formula (c-5) or its salt is a cyan or substantially cyan dye. "The compound represented by formula (c-5) or its salt" may hereinafter be referred to simply as "a (c-5) dye."

The third ink may contain other cyan or substantially cyan dyes. Examples of such extra cyan or substantially cyan dyes include C.I. Direct Blue 1, 2, 15, 71, 86, 87, 98, 165, 199, and 202.

Even when any such cyan or substantially cyan dye is contained in the third ink, it remains preferred, in light of the area of the gamut, to ensure that the total percentage of (c-1) to (c-5) dyes in the third ink is 40.0% by mass or more and 99.0% by mass or less of the total mass of dyes in the third ink.

1.3.2. Extra Ingredients

The third ink according to this embodiment may contain a surfactant, an organic solvent, water, and other ingredients. These ingredients are as described in the above section of First Ink and are not discussed again.

1.4. Characteristics of the Inks and Other Information

The first, second, and third inks are attached to a recording medium, such as paper, film, or fabric, preferably by ink jet technology. It is therefore preferred to ensure that the viscosity of each ink is 1.5 mPa·s or more and 15.0 mPa·s or less, more preferably 1.5 mPa·s or more and 5.0 mPa·s or less, even more preferably 1.5 mPa·s or more and 3.6 mPa·s or less at 20° C. Attaching the inks to a recording medium by ink jet technology is an easy way to form a predetermined image efficiently.

The first, second, and third inks preferably have a surface tension at 25.0° C. of 40.0 mN/m or less, preferably 38.0 mN/m or less, more preferably 35.0 mN/m or less, even more preferably 30.0 mN/m or less. This ensures moderate wetting and spread on a recording medium. As for measurement, the surface tension can be measured by wetting a platinum plate with the composition and checking the surface tension under 25.0° C. conditions using CBVP-Z automated surface tensiometer (trade name, Kyowa Interface Science Co., Ltd.).

2. Examples and Comparative Examples

The following describes an aspect of the present disclosure in detail by providing examples, but no aspect of the disclosure is limited to these Examples. In the following, "parts" and "%" are by mass unless stated otherwise.

2.1. Preparation of Dye Inks

Yellow dye inks Y1 to Y15 having different formulae were prepared according to the formulae presented in Table 1, magenta dye inks M1 to M9 having different formulae were prepared according to the formulae presented in Table 2, and cyan dye inks C1 to C9 having different formulae were prepared according to the formulae presented in Table 3. Each ink was prepared by putting its ingredients, specified in any of Tables 1 to 3, into a container, mixing the ingredients by stirring them for 2 hours with a magnetic stirrer, and then filtering the mixture through a 5-μm membrane filter to remove impurities, such as dust and coarse particles. The values in Tables 1 to 3 are all in % by mass, and the purified water was added to make the total mass of the ink 100%.

TABLE 1

| | Name | Y-1 | Y-2 | Y-3 | Y-4 | Y-5 | Y-6 | Y-7 | Y-8 | Y-9 | Y-10 | Y-11 | Y-12 | Y-13 | Y-14 | Y-15 |
|---|---|---|---|---|---|---|---|---|---|---|---|---|---|---|---|---|
| Yellow dye(s) | (y-1) | 2.0 | 2.0 | 2.0 | 2.0 | 4.0 | 2.0 | 2.0 | 2.0 | | | | | | | |
| | (y-2) | 2.0 | 1.0 | 1.0 | 1.0 | | | | | 4.0 | 2.0 | 2.0 | 2.0 | | | |
| | (y-3) | | 1.0 | | | | 2.0 | | | | 2.0 | | | 4.0 | | |
| | (y-4) | | | 1.0 | | | | 2.0 | | | | 2.0 | | | 4.0 | |
| | (y-5) | | | | 1.0 | | | | 2.0 | | | | 2.0 | | | 4.0 |
| Surfactants | Surfynol 104PG50 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| | OLFINE E1010 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 |
| Organic solvents | Triethylene glycol | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 |
| | Triethylene glycol monobutyl ether | 7.0 | 7.0 | 7.0 | 7.0 | 7.0 | 7.0 | 7.0 | 7.0 | 5.0 | 7.0 | 7.0 | 7.0 | 7.0 | 7.0 | 7.0 |
| | Glycerol | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 |
| Others | Triethanolamine | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| | PROXEL | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| | EDTA | 0.02 | 0.02 | 0.02 | 0.02 | 0.02 | 0.02 | 0.02 | 0.02 | 0.02 | 0.02 | 0.02 | 0.02 | 0.02 | 0.02 | 0.02 |
| | Purified water | Balance | Balance | Balance | Balance | Balance | Balance | Balance | Balance | Balance | Balance | Balance | Balance | Balance | Balance | Balance |

TABLE 2

| | Name | Magenta | | | | | | | | |
|---|---|---|---|---|---|---|---|---|---|---|
| | | M-1 | M-2 | M-3 | M-4 | M-5 | M-6 | M-7 | M-8 | M-9 |
| Magenta dye(s) | (m-1) | 4.0 | | | | 2.0 | 2.0 | 2.0 | 2.0 | |
| | (m-2) | | 4.0 | | | 2.0 | | | | |
| | (m-3) | | | 4.0 | | | 2.0 | | | |
| | (m-4) | | | | 4.0 | | | 2.0 | | |
| | (m-5) | | | | | | | | 2.0 | 4.0 |
| Surfactants | Surfynol 104PG50 | 0.2 | 0.2 | 0.2 | 0.2 | 0.2 | 0.2 | 0.2 | 0.2 | 0.2 |
| | OLFINE E1010 | 0.3 | 0.3 | 0.3 | 0.3 | 0.3 | 0.3 | 0.3 | 0.3 | 0.3 |
| Organic solvents | Triethylene glycol | 10.0 | 10.0 | 10.0 | 10.0 | 10.0 | 10.0 | 10.0 | 10.0 | 10.0 |
| | Triethylene glycol monobutyl ether | 7.0 | 7.0 | 7.0 | 7.0 | 7.0 | 7.0 | 7.0 | 7.0 | 7.0 |
| | Glycerol | 10.0 | 10.0 | 10.0 | 10.0 | 10.0 | 10.0 | 10.0 | 10.0 | 10.0 |
| Others | Triethanolamine | 0.5 | 0.5 | 0.5 | 0.5 | 0.5 | 0.5 | 0.5 | 0.5 | 0.5 |
| | PROXEL | 0.1 | 0.1 | 0.1 | 0.1 | 0.1 | 0.1 | 0.1 | 0.1 | 0.1 |
| | EDTA | 0.02 | 0.02 | 0.02 | 0.02 | 0.02 | 0.02 | 0.02 | 0.02 | 0.02 |
| | Purified water | Balance | Balance | Balance | Balance | Balance | Balance | Balance | Balance | Balance |

TABLE 3

| | Name | Cyan | | | | | | | | |
|---|---|---|---|---|---|---|---|---|---|---|
| | | C-1 | C-2 | C-3 | C-4 | C-5 | C-6 | C-7 | C-8 | C-9 |
| Cyan dye(s) | (c-1) | 4.0 | | | | 2.0 | 2.0 | 2.0 | 2.0 | |
| | (c-2) | | 0.4 | | | 0.2 | | | | |
| | (c-3) | | 3.6 | | | 1.8 | | | | |
| | (c-4) | | | 4.0 | | | 2.0 | | | |
| | (c-5) | | | | 4.0 | | | 2.0 | | |
| | (c-6) | | | | | | | | 2.0 | 4.0 |
| Surfactants | Surfynol 104PG50 | 0.2 | 0.2 | 0.2 | 0.2 | 0.2 | 0.2 | 0.2 | 0.2 | 0.2 |
| | OLFINE E1010 | 0.3 | 0.3 | 0.3 | 0.3 | 0.3 | 0.3 | 0.3 | 0.3 | 0.3 |
| Organic solvents | Triethylene glycol | 10.0 | 10.0 | 10.0 | 10.0 | 10.0 | 10.0 | 10.0 | 10.0 | 10.0 |
| | Triethylene glycol monobutyl ether | 7.0 | 7.0 | 7.0 | 7.0 | 7.0 | 7.0 | 7.0 | 7.0 | 7.0 |
| | Glycerol | 10.0 | 10.0 | 10.0 | 10.0 | 10.0 | 10.0 | 10.0 | 10.0 | 10.0 |
| Others | Triethanolamine | 0.5 | 0.5 | 0.5 | 0.5 | 0.5 | 0.5 | 0.5 | 0.5 | 0.5 |
| | PROXEL | 0.1 | 0.1 | 0.1 | 0.1 | 0.1 | 0.1 | 0.1 | 0.1 | 0.1 |
| | EDTA | 0.02 | 0.02 | 0.02 | 0.02 | 0.02 | 0.02 | 0.02 | 0.02 | 0.02 |
| Purified water | | Balance | Balance | Balance | Balance | Balance | Balance | Balance | Balance | Balance |

Major ingredients in Tables 1 to 3 were as follows.
(y-1) to (y-3): (y-1) to (y-3) dyes as described above. Sodium salts.
(y-4) was the compound represented by formula (y-4) below.

[Chem. 26]

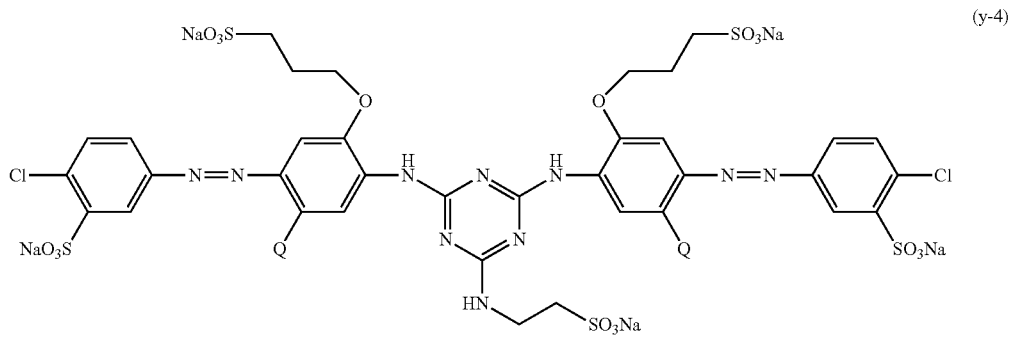

(y-4)

(y-5) was the compound represented by formula (y-5) below.

[Chem. 27]

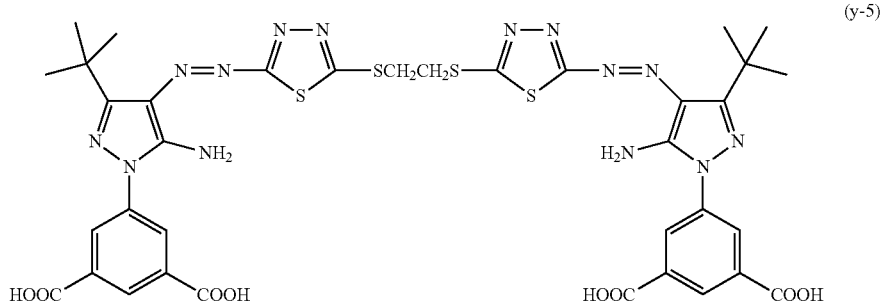

(y-5)

(m-1) to (m-3): (m-1) to (m-3) dyes as described above. (m-1) was a sodium salt, (m-2) was a lithium and sodium salt, and (m-3) was a sodium salt. (m-3), furthermore, satisfied the following:

(In formula (m-3), $R^1$, $R^5$, $R^6$, and $R^{10}$ each independently represent an alkyl group. $R^3$ and $R^8$ each independently represent a hydrogen atom, an alkyl group, an alkoxy group, or an aryloxy group, and an alkyl group, an alkoxy group, and an aryloxy group may have at least one type of substituent selected from the group of types of substituents consisting of alkyl, aryl, arylalkyl, hydroxyl, carbamoyl, sulfamoyl, alkoxy, cyano, halogen, and ionic groups. $R^2$, $R^4$, $R^7$, and $R^9$ each independently represent a hydrogen atom or an acylamino group represented by formula (m-3'), with at least one of $R^2$, $R^4$, $R^7$, and $R^9$ being an acylamino group represented by formula (m-3'). Z represents a $SO_3H$ group, $SO_3M$ group (where M represents an ammonium ion or alkali metal ion), or sulfamoyl group. n represents an integer of 0 to 3 when at least one of $R^2$, $R^3$, $R^4$, $R^7$, $R^8$, and $R^9$ is substituted with an ionic group, and an integer of 1 to 3 when not, and Z, when present, is in place of at least one aromatic hydrogen atom.)

(In formula (m-3'), $R^{11}$ represents an alkyl group, a cycloalkyl group, an aryl group, an arylalkyl group, an alkenyl group, or a heterocyclic group, and an alkyl group, a cycloalkyl group, an aryl group, an arylalkyl group, an alkenyl group, and a heterocyclic group may have at least one type of substituent selected from the group of types of substituents consisting of alkyl, aryl, arylalkyl, alkenyl, alkoxy, cyano, alkylamino, sulfoalkyl, carbamoyl, sulfamoyl, sulfonylamino, halogen, and ionic groups. *represents a site for binding with the aromatic ring(s) in formula (m-3))

(m-4) was a lithium salt of a (m-4) dye as described above.

(m-5) was a compound represented by formula (m-5) below.

[Chem. 28]

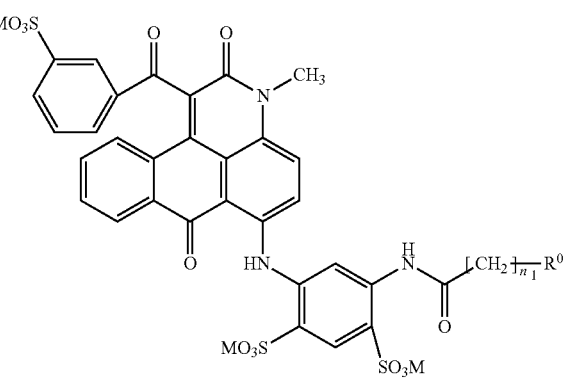

(m-5)

(m-5) satisfied the following:

(In formula (m-5), $n_1$ is 1 or 2; each of the three Ms is sodium or ammonium; the three Ms may be the same or different; and $R^0$ is a C1 to C8 monoalkylamino group substituted with a carboxy group.)

(c-1) to (c-5): (c-1) to (c-5) dyes as described above. (c-1) to (c-3) were sodium salts.

(c-6) was a compound represented by formula (c-6) below.

[Chem. 29]

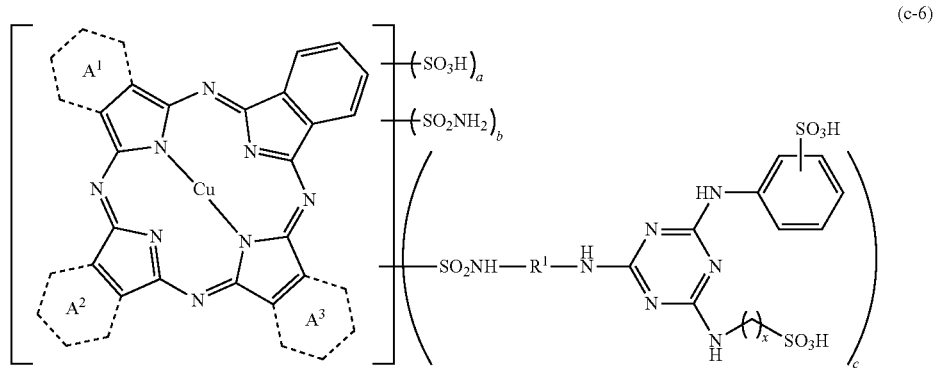

(c-6) satisfied the following:
(In formula (c-6), rings $A^1$, $A^2$, and $A^3$ are each selected from a benzene ring, a 2,3-pyridine ring, and a 3,2-pyridine ring, with at least one of rings $A^1$, $A^2$, and $A^3$ being a 2,3-pyridine ring or 3,2-pyridine ring, and rings $A^1$, $A^2$, and $A^3$ may be the same or different; $1.0 \leq a \leq 3.0$, $0.2 \leq b \leq 1.8$, $0.8 \leq c \leq 1.6$, and $0 \leq a+b+c \leq 4$; $1 \leq x \leq 3$, where x is an integer; and $R^1$ is a C1 to C6 linear alkylene group.)

Surfynol 104PG50: (trade name, Air Products and Chemicals): An acetylene glycol surfactant
OLFINE E1010: (trade name, Nissin Chemical Industry): An acetylene glycol surfactant
PROXEL: PROXEL XL2: (trade name, Lonza): An antimold/preservative
EDTA: Disodium ethylenediaminetetraacetate (reagent): A chelating agent 2.2. Testing 2.2.1. Color Strength (Gamut) of the Ink Sets The ink set of each Example or Comparative Example in Table 4 was loaded into an ink jet printer (trade name "EW-M660FT," Seiko Epson Corporation), and patches in primary/secondary colors were printed on printing paper (Xerox 4200, trade name; Fuji Xerox). The OD and Lab were measured, and the gamut volume was calculated. The printing conditions were 25° C. and 40% RH. Color strength was graded according to the evaluation criteria below. The test results are presented in Tables 4.

A: The gamut volume is 160000 or more.
B: The gamut volume is 155000 or more and less than 160000.
C: The gamut volume is 150000 or more and less than 155000.
D: The gamut volume is less than 150000.

2.2.2. Recovery from Clogging (Resistance to Clogging) of the Ink Sets

Each ink set in Table 4 was loaded into an ink jet printer (trade name "EW-M660FT," Seiko Epson Corporation). While a print job was in progress, the printer was turned off to make the ink jet head exposed to the environment without being capped. After the ink jet head was left under 40° C. and 40% RH conditions for 1 week, the number of cleaning operations required until normal ejection was counted. Clogging resistance was graded according to the criteria below. The results are presented in Table 4.

A: One cleaning operation
B: Two cleaning operations
C: Three cleaning operations
D: Four or more cleaning operations

TABLE 4

|  |  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| Ink set | Yellow | Y-1 | Y-2 | Y-3 | Y-4 | Y-5 | Y-6 | Y-7 | Y-8 | Y-1 | Y-1 | Y-1 |
|  | Magenta | M-1 | M-1 | M-1 | M-1 | M-1 | M-1 | M-1 | M-1 | M-2 | M-3 | M-4 |
|  | Cyan | C-1 | C-1 | C-1 | C-1 | C-1 | C-1 | C-1 | C-1 | C-1 | C-1 | C-1 |
| Grades of the ink set | Color strength | A | A | A | A | C | B | B | B | C | C | B |
|  | Clogging resistance | A | B | C | A | C | C | C | B | B | B | B |

|  |  | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| Ink set | Yellow | Y-1 | Y-1 | Y-1 | Y-1 | Y-1 | Y-1 | Y-1 | Y-1 | Y-1 | Y-1 | Y-1 |
|  | Magenta | M-5 | M-6 | M-7 | M-8 | M-1 | M-1 | M-1 | M-1 | M-1 | M-1 | M-1 |
|  | Cyan | C-1 | C-1 | C-1 | C-1 | C-2 | C-3 | C-4 | C-5 | C-6 | C-7 | C-8 |
| Grades of the ink set | Color strength | A | A | A | C | B | B | B | A | A | A | C |
|  | Clogging resistance | B | B | A | B | B | B | B | A | A | A | B |

| | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| Ink set Yellow | Y-9 | Y-10 | Y-11 | Y-12 | Y-13 | Y-14 | Y-15 | Y-1 | Y-1 |
| Magenta | M-1 | M-1 | M-1 | M-1 | M-1 | M-1 | M-1 | M-9 | M-1 |
| Cyan | C-1 | C-1 | C-1 | C-1 | C-1 | C-1 | C-1 | C-1 | C-9 |
| Grades of the ink set Color strength | D | D | C | D | D | D | D | D | D |
| Clogging resistance | C | B | D | B | C | D | C | B | B |

2.3. Test Results

As shown in Table 4, the ink sets of Examples, each including a yellow ink (first ink) containing a (y-1) dye, a magenta ink (second ink) containing one or two or more of the (m-1) dyes, the (m-2) dyes, the (m-3) dyes, and the (m-4) dyes, and a cyan ink (third ink) containing one or two or more of the (c-1) dyes, the (c-2) dyes, the (c-3) dyes, the (c-4) dyes, and the (c-5) dyes, achieved high color strength (gamut volume) and were good in recovery from clogging.

The present disclosure is not limited to the above embodiments, and many variations are possible. For example, the present disclosure embraces configurations substantially identical to those described in the embodiments (e.g., configurations identical in function, methodology, and results to or having the same goal and offering the same advantages as the described ones). The present disclosure also includes configurations created by changing any nonessential part of those described in the above embodiments. Furthermore, the present disclosure encompasses configurations identical in operation and effect to or capable of fulfilling the same purposes as those described in the above embodiments. Configurations obtained by adding any known technology to those described in the embodiments are also part of the present disclosure.

What is claimed is:

1. An ink set comprising:

a first ink containing a compound comprising formula (y-1) below or a salt thereof;

[Chem. 1]

(y-1)

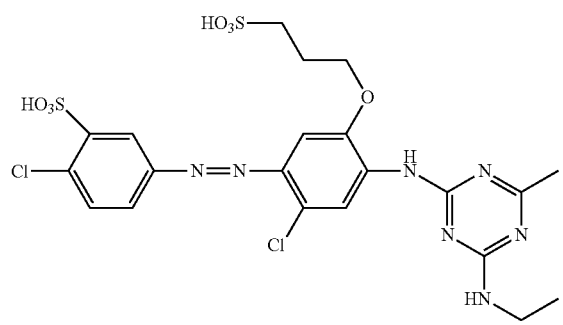

a second ink containing one or two or more of:

a compound comprising formula (m-1) below or a salt thereof;

[Chem. 2]

(m-1)

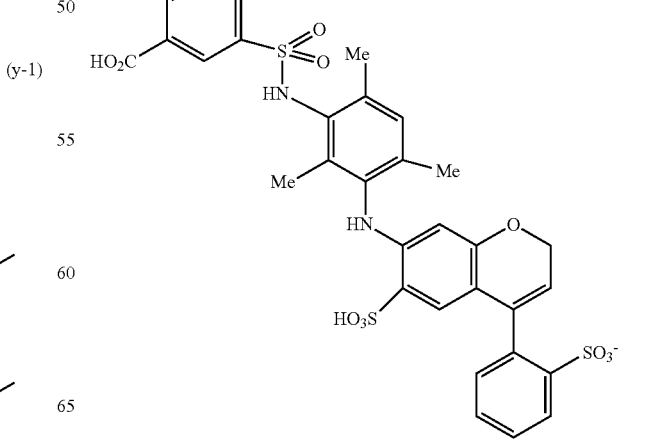

-continued

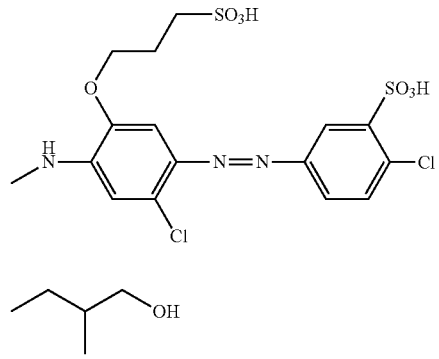

-continued

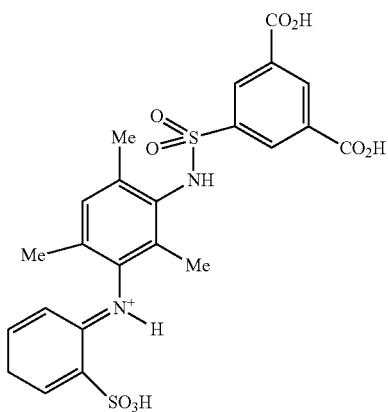

a compound comprising formula (m-2) below or a salt thereof;

[Chem. 3]

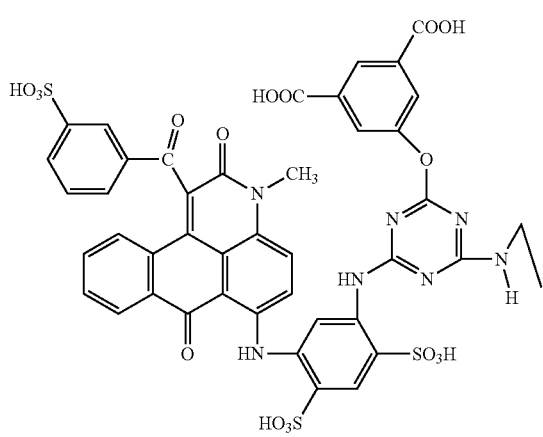
(m-2)

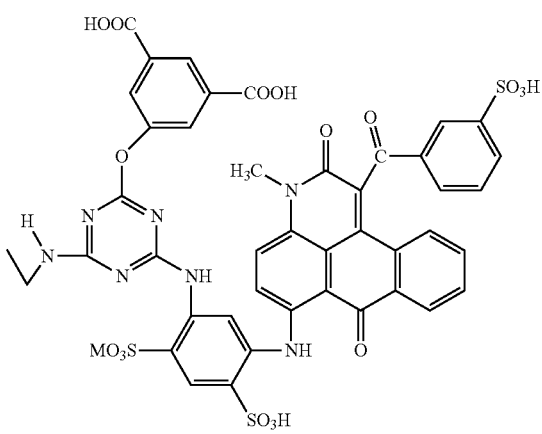

a compound comprising formula (m-3) below or a salt thereof,

[Chem. 4]

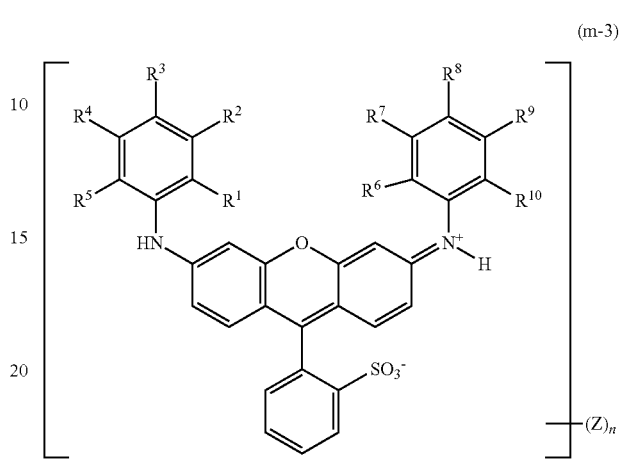
(m-3)

where $R^1$, $R^5$, $R^6$, and $R^{10}$ each independently represent an alkyl group; $R^3$ and $R^8$ each independently represent a hydrogen atom, an alkyl group, an alkoxy group, or an aryloxy group, and an alkyl group, an alkoxy group, and an aryloxy group may have at least one type of substituent selected from the group of types of substituents consisting of alkyl, aryl, arylalkyl, hydroxyl, carbamoyl, sulfamoyl, alkoxy, cyano, halogen, and ionic groups; $R^2$, $R^4$, $R^7$, and $R^9$ each independently represent a hydrogen atom or an acylamino group comprising formula (m-3') below, with at least one of $R^2$, $R^4$, $R^7$, and $R^9$ being an acylamino group comprising formula (m-3') below; Z represents a $SO_3H$ group, $SO_3M$ group, where M represents an ammonium ion or alkali metal ion, or sulfamoyl group; n represents an integer of 0 to 3 when at least one of $R^2$, $R^3$, $R^4$, $R^7$, $R^8$, and $R^9$ is substituted with an ionic group, and an integer of 1 to 3 when not, and Z, when present, is in place of at least one aromatic hydrogen atom,

[Chem. 5]

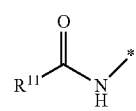
(m-3')

where $R^{11}$ represents an alkyl group, a cycloalkyl group, an aryl group, an arylalkyl group, an alkenyl group, or a heterocyclic group, and an alkyl group, a cycloalkyl group, an aryl group, an arylalkyl group, an alkenyl group, and a heterocyclic group may have at least one type of substituent selected from the group of types of substituents consisting of alkyl, aryl, arylalkyl, alkenyl, alkoxy, cyano, alkylamino, sulfoalkyl, carbamoyl, sulfamoyl, sulfonylamino, halogen, and ionic groups; and * represents a site for binding with the aromatic ring or rings in formula (m-3); and a compound comprising formula (m-4) below or a salt thereof; and

[Chem. 6]

(m-4)

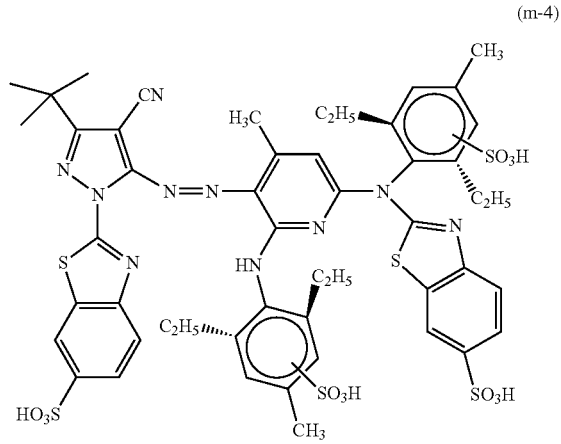

a third ink containing one or two or more of:
a compound comprising formula (c-1) below or a salt thereof,

[Chem. 7]

(c-1)

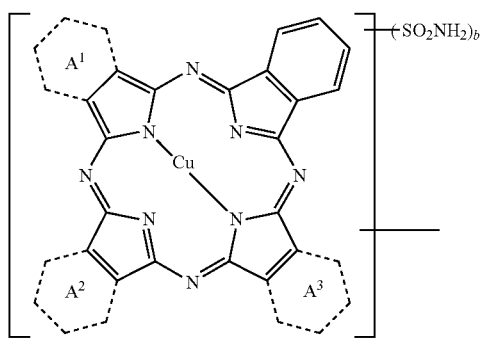

where 0≤b≤a, 0≤c≤4, and 1≤(b+c)≤4, where b+c represents an integer; and rings $A^1$, $A^2$, and $A^3$ are each selected from a benzene ring, a 2,3-pyridine ring, and a 3,2-pyridine ring, with at least one of rings $A^1$, $A^2$, and $A^3$ being a 2,3-pyridine ring or 3,2-pyridine ring, and rings $A^1$, $A^2$, and $A^3$ may be the same or different;

a compound comprising formula (c-2) below or a salt thereof;

[Chem. 8]

(c-2)

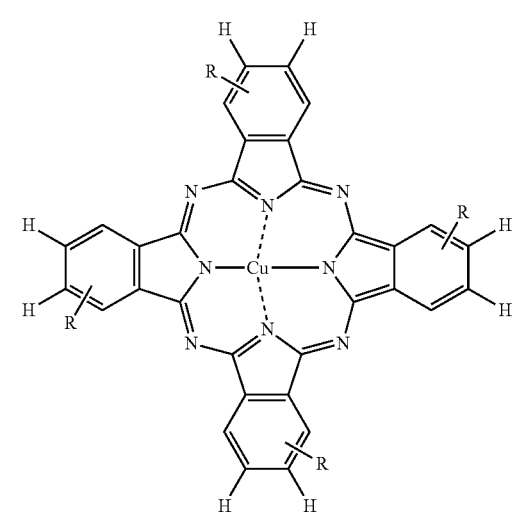

$R = $ —$SO_2(CH_2)_3SO_3H$ a compound comprising formula (c-3) below or a salt thereof;

[Chem. 9]

(c-3)

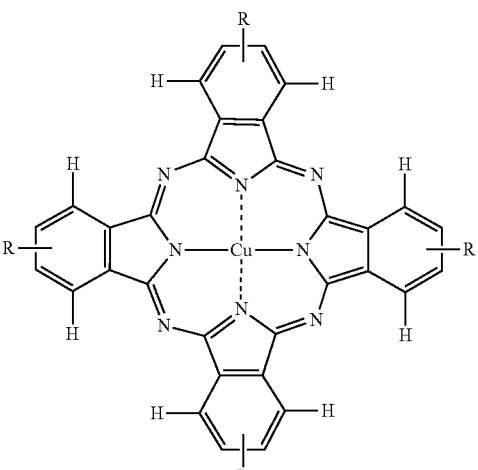

$R = $ —$SO_2(CH_2)_3SO_3H$/ —$SO_2(CH_2)_3SO_2NHCH_2CH(OH)CH_3$

[2/2]

a compound comprising formula (c-4) below or a salt thereof,

[Chem. 10]

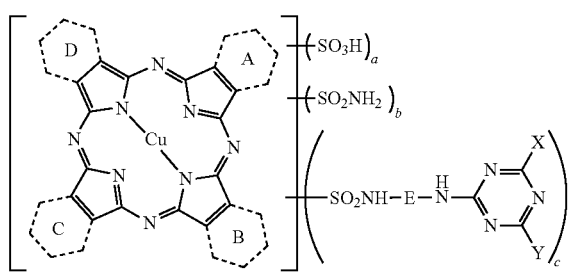

(c-4)

where rings A, B, C, and D are each independently an aromatic six-membered ring, with at least one of rings A, B, C, and D being a pyridine ring or pyrazine ring; E is an alkylene group; X is a sulfo-substituted anilino group, carboxy-substituted anilino group, or phosphono-substituted anilino group, and the substituted anilino group may further have one to four substituents selected from the group consisting of a sulfonic acid group, a carboxy group, a phosphono group, a sulfamoyl group, a carbamoyl group, a hydroxy group, an alkoxy group, an amino group, an alkylamino group, a dialkylamino group, an arylamino group, a diarylamino group, an acetylamino group, a ureido group, an alkyl group, a nitro group, a cyano group, a halogen, an alkylsulfonyl group, and an alkylthio group; Y is a hydroxy group or amino group; and $0.0 \leq a \leq 2.0$, $0.0 \leq b \leq 3.0$, $0.1 \leq c \leq 3.0$, and $1.0 \leq a+b+c \leq 4.0$; and a compound comprising formula (c-5) below or a salt thereof.

[Chem. 11]

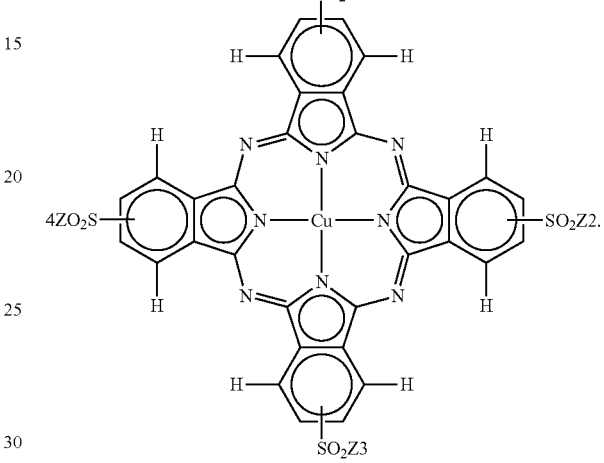

(c-5)

$Z1 = Z2 = Z3 = $ ——$(CH_2)_3SO_3H$
$Z4 = $ ——$(CH_2)_3SO_3NHCH_2CH(OH)CH_3$

2. The ink set according to claim 1, wherein
the first ink further contains a compound comprising formula (y-2) below or a salt thereof.

[Chem. 12]

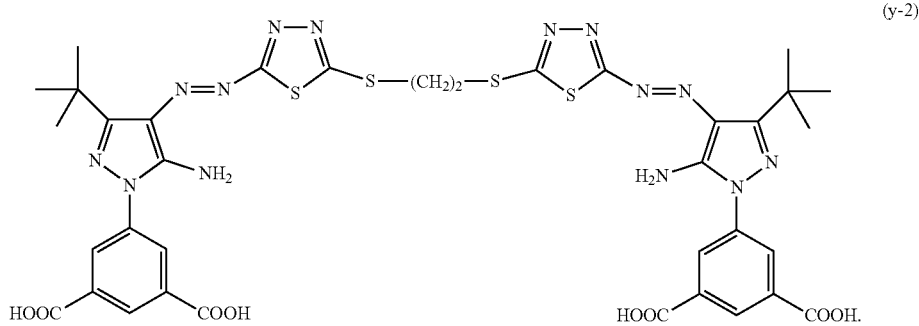

(y-2)

3. The ink set according to claim 1, wherein the second ink contains the compound comprising formula (m-2) or a salt thereof.

4. The ink set according to claim 1, wherein the third ink contains the compound comprising formula (c-2) or a salt thereof and the compound comprising formula (c-3) or a salt thereof.

* * * * *